United States Patent
Venkatraman et al.

(10) Patent No.: US 9,987,399 B2
(45) Date of Patent: Jun. 5, 2018

(54) NON-BIODEGRADABLE STENT COMPRISING A BIODEGRADABLE COATING AND METHOD OF COATING THE SAME

(75) Inventors: Subramanian Venkatraman, Singapore (SG); Yin Chiang Boey, Singapore (SG); Laxmikant Khanolkar, Mumbai (IN)

(73) Assignee: Nanyang Technological University, Singapore (SG)

(*) Notice: Subject to any disclaimer, the term of this patent is extended or adjusted under 35 U.S.C. 154(b) by 660 days.

(21) Appl. No.: 12/740,638

(22) PCT Filed: Oct. 30, 2008

(86) PCT No.: PCT/SG2008/000413
§ 371 (c)(1),
(2), (4) Date: Jul. 21, 2010

(87) PCT Pub. No.: WO2009/058098
PCT Pub. Date: May 7, 2009

(65) Prior Publication Data
US 2010/0305689 A1    Dec. 2, 2010

Related U.S. Application Data

(60) Provisional application No. 60/983,648, filed on Oct. 30, 2007.

(51) Int. Cl.
*A61F 2/82*     (2013.01)
*A61L 31/14*    (2006.01)
(Continued)

(52) U.S. Cl.
CPC .............. *A61L 31/141* (2013.01); *A61F 2/91* (2013.01); *A61L 31/10* (2013.01);
(Continued)

(58) Field of Classification Search
CPC ........................................................ A61F 2/82
(Continued)

(56) References Cited

U.S. PATENT DOCUMENTS

2006/0058868 A1    3/2006  Gale
2007/0196423 A1*   8/2007  Ruane et al. ................ 424/423

FOREIGN PATENT DOCUMENTS

EP    1 470 828    10/2004
EP    1 974 756    10/2008
(Continued)

OTHER PUBLICATIONS

Wang, et al., "Controlled release of sirolimus from a multilayered PLGA stent matrix," *Biomaterials*, 27: 5588-5595 (2006).
(Continued)

*Primary Examiner* — Matthew Schall
(74) *Attorney, Agent, or Firm* — Pabst Patent Group LLP (57) ABSTRACT

The present invention relates to the field of non-biodegradable stents, and therein to non-biodegradable stents coated with at least one layer of a biodegradable polymer which maintains mechanical integrity of the coating both in storage and upon balloon expansion and which can optionally release drugs. The at least one polymer layer comprises a biodegradable polymer and a plasticizer. The present invention also relates to a manufacturing method of such a non-biodegradable stent.

28 Claims, 4 Drawing Sheets

(51) Int. Cl.
    *A61F 2/91*          (2013.01)
    *A61L 31/10*        (2006.01)
    *A61F 2/30*          (2006.01)

(52) U.S. Cl.
    CPC ............... *A61F 2002/30064* (2013.01); *A61F 2250/0067* (2013.01); *A61F 2310/0097* (2013.01); *A61L 2420/08* (2013.01)

(58) Field of Classification Search
    USPC ........................................................ 623/1.46
    See application file for complete search history.

(56) References Cited

FOREIGN PATENT DOCUMENTS

| | | |
|---|---|---|
| JP | 2007-097706 | 4/2007 |
| WO | WO 97/047254 | 12/1997 |
| WO | WO 05/087266 | 9/2005 |

OTHER PUBLICATIONS

Wormuth, et al., "Morphological changes as drug elutes from biodegradable coatings," *Microsc. Microanal.*, 13(Suppl. 2): 1690-1 (2008).

European Search Report for correlating European Applications EP 15184596 dated Dec. 22, 2015.

\* cited by examiner

Failure of coatings after crimping and expansion (no TEC)

Figure 3B

TEC-containing coated stent after crimping and expansion

NON-BIODEGRADABLE STENT COMPRISING A BIODEGRADABLE COATING AND METHOD OF COATING THE SAME

CROSS-REFERENCE TO RELATED APPLICATIONS

The present application is a filing under 35 U.S.C. § 371 of PCT/SG2008/000413 filed with the Singapore Receiving Office of the Patent Cooperation Treaty on Oct. 30, 2008, which claims the benefit of U.S. provisional application No. 60/983,648 filed on Oct. 30, 2007, the content of which is incorporated herein by reference in its entirety for all purposes.

FIELD OF THE INVENTION

The present invention generally relates to the field of non-biodegradable stents, and therein to non-biodegradable stents coated with at least one layer of a biodegradable coating composition which maintains mechanical integrity both in storage and upon balloon expansion and which can optionally release drugs.

BACKGROUND OF THE INVENTION

Stents with the capability of drug elution can address different problems associated with coronary or peripheral vascular blockages. Conventionally, the drug is contained in a polymer coating which covers the stent and can be released from this polymer coating after the stent has been placed into the subject to be treated. Generally, conventional drug-containing coatings are for example liable to delaminations, especially during stent expansion. However, in case of a delamination of the drug-containing coating, the drug cannot be delivered to the desired location or in the desired amount. Therefore, it is important for such drug containing coatings to be able to maintain their mechanical integrity during storage and especially after stent expansion using a balloon.

Conventionally coated metal stents generally use a primer coating, typically a parylene coating, prior to the coating with bio-degradable polymer combinations in order to avoid delaminations of the coating during stent expansion. Such a primer coating is deemed essential to prevent delamination of the bio-degradable polymer coating from the metal surface, both during storage and upon balloon expansion. In cases where the polymer coating comprises a drug component, delaminations are more likely. Thus, a primer coating is generally used in order to eliminate the problems with mechanical integrity, but the primer coatings such as the parylene coatings which are generally used are, however, non-biodegradable and increase the overall coating thickness because the primer coating generally does not accommodate any drug.

Stents with poly(lactic-co-glycolic acid) (PLGA) polymer coatings have recently been described by Wormuth et al. for preventing arteries from collapsing. These coatings are capable of releasing a drug, e.g. an antiproliferative drug such as rapamycin (Wormuth et al. in Microsc. Microanal. 13 (Suppl. 2), 2008, 1690-1691). The polymer coating is based on a biodegradable polymer made of poly(lactic-co-glycolic acid) (PLGA) and comprises the drug in a concentration in the range from 5 to 50 wt %. Alternative drug-loaded polylactic acid (PLA)/polycaprolactone (PCL) polymer coatings are known to have drawbacks such as a limited thickness of the coating, which is not able to sustain the drug release over a long period, and neither is it able to control the release to any great extent. Drug loading in these coatings need to be low in order to avoid adverse embrittlement and delamination of the biodegradable polymer coating from the metal substrate.

On that basis it was recently suggested to solve the above problems by using fully bio-degradable stents which have a potential for carrying and delivering much higher drug loadings. In this case, the metal stent was replaced by a polymer stent in order to eliminate the delamination drawbacks of the conventional polymer coated non-biodegradable stents. Since in polymer stents, no primer layer is necessary anymore, the polymer coating can be made thicker compared to the polymer coating used with metal stents and, thus, a higher drug loading is possible (Wang et al. in Biomaterials 27 (2006), 5588-5595). However, such stents can only be used in temporary applications due to the fully biodegradability of the polymeric stent material and the polymer coating.

In view of the above it is desirable to have drug loaded stents that are able to sustain the drug release over a long period and/or that are able to control the release of drugs.

SUMMARY OF THE INVENTION

According to a first aspect of the present invention, a non-biodegradable stent is provided, wherein the stent comprises a biodegradable coating wherein said coating comprises at least one polymer layer (i.e. one or more polymer layers) comprising a biodegradable polymer and a plasticizer.

A second aspect of the present invention relates to a method for manufacturing a coated non-biodegradable stent, wherein the method comprises coating the non-degradable stent with a mixture comprising a biodegradable polymer and a plasticizer.

Embodiments are described in the dependent claims and other aspects and features of the invention will also become apparent from the following description of specific embodiments and non-limiting examples of the present invention.

BRIEF DESCRIPTION OF THE FIGURES

The present invention will be better understood with reference to the detailed description when considered in conjunction with the accompanying drawings.

FIGS. 3A and 3B are photographs of coated stents according to the invention made with a scanning electron microscope, wherein FIG. 3A shows coatings without a plasticizer and FIG. 3B shows coatings with TEC containing coatings.

DETAILED DESCRIPTION OF THE INVENTION

Stents, which are generally open tubular structures, have become increasingly important in medical procedures to restore the function of body lumens. Non-biodegradable stents can, for example, be used for addressing different problems associated with coronary or peripheral vascular blockages and are for example used in translumenal procedures such as angioplasty to restore an adequate blood flow to the heart. Especially in this field, the stents should be non-biodegradable as coronary or peripheral vascular blockages should be prevented for the remaining lifetime of the subject to be treated. In order to avoid a phenomenon such as restenosis, i.e. the re-blockage of an artery due to formation of scar tissue, stents are usually coated with a polymer coating which can release, e.g., an antiproliferative drug. For example, the polymer coating can control the elution of the drug. The release of the drug may also be accomplished by controlled degradation of the polymer coating. After drug elution the polymer coating should be biodegraded within the body in order to avoid any deleterious effects generally associated with decomposition reactions of polymer compounds in vivo.

The stents disclosed here comprise a coating with at least one layer comprising a biodegradable polymer coating and a plasticizer. That means that the coating can comprise one or more layers of a biodegradable polymer in which at least in one layer, e.g. the layer in contact with the stent material, or in two or more layers, one or more plasticizer(s) are contained. It has been found herein that these stents, when loaded with a drug (that is included in the one or more layers of the coating) provide a controlled release of the drug and at the same time the polymer coating maintains mechanical integrity, for example, during storage and upon balloon expansion. It has also been found herein that such coating does not need a primer coating. As a primer coating is not required, the overall thickness of the polymer coating can be made thinner compared to the conventional primer coatings. In addition the entire coating can be made of bio-degradable material(s) and an optional drug loading can be made higher because the drug can be contained in the total coating layer.

In line with the above, the term "stent" as used herein refers to a prosthesis, usually a slotted tube or a helical coil or a wire mesh tube, designed to be inserted into a vessel or passageway of a subject (usually a mammal such a human, dog, mouse, rat, etc) to be treated to keep it open. A stent of the invention can for example be inserted into narrowed coronary arteries to help keep them open after balloon angioplasty. When used for this purpose, the stent then allows the normal flow of blood and oxygen to the heart. A stent of the invention can also be placed in narrowed carotid arteries (the vessels in the front of the neck that supply blood to the brain) in order to treat patients at elevated risk for stroke. In addition, a stent of the invention can also be used in other body parts such as the esophagus to treat a constriction, or ureters to maintain the drainage of urine from the kidneys, or the bile duct to keep it open.

The non-biodegradable stents described herein may include or be of any desired non-biodegradable material as long as the material provides rigidity that is sufficiently high for the desired application of the stent and provides a sufficient peel adhesion to the coating composition. Furthermore, the material should be biocompatible and should be biostable within the body or by the impact of the ambience, such as exposure to light, moisture, elevated temperature and/or air. Illustrative examples of suitable stent materials are metals, metal alloys, or biostable polymers. Examples of suitable metal alloys include, but are not limited to stainless steel (e.g. stainless style of type 310 SS or of type 316 L using the definition of the American Iron and Steel Institute), or cobalt alloys, including cobalt chromium alloys and cobalt-chromium-nickel alloys (including, e.g. elgiloy etc.), titanium alloys (including nitinol), chromium alloys, and magnesium alloys including, e.g., magnesium alloys comprising yttrium or rare earth metals. Examples of metals that can be used as stent material include precious metals including gold, platinum or palladium, or transition metals such as tantalum, titanium or niobium. Suitable nonmetallic biocompatible materials include, but are not limited to, polyamides, polyurethanes, polyolefins (i.e. polypropylene, polyethylene etc.), and nonabsorbable polyesters (e.g. polyethylene terephthalate). Further examples of nonmetallic materials are shape memory polymers such as polymers on the basis of oligo(caprolactone)diol/p-dioxanone copolymers, etc.

The stent used herein may be a rigid stent such as one that is generally used in the implantation in coronary arteries. Alternatively, a flexible stent which can, for example, be introduced into blood vessels which need to be flexible because of their location in the body, for example at a joint such as the knee, etc., can also be used herein. A flexible stent of the invention may also be suited for use in the esophagus or in the urethra tract. The term "flexible" means that the stent can be temporarily flexed or bound, but generally maintains its tubular structure such that the stent can, for example, be used in blood vessels near a joint or in lumens which need to be flexible.

In the context of the present invention the term "biodegradable polymer coating" refers to a coating comprising one or more polymer components that can be completely removed from a localized area by physiological metabolic processes such as resorption. A "biodegradable" compound can, when taken up by a cell, be broken down into components by cellular machinery such as lysosomes or by hydrolysis that the cells can either reuse or dispose of without significant toxic effect on the cells. Examples of biodegradation processes include enzymatic and non-enzymatic hydrolysis, oxidation and reduction. Suitable conditions for non-enzymatic hydrolysis, for example, include exposure of biodegradable material to water at a temperature and a pH of a lysosome (i.e. the intracellular organelle). The degradation fragments typically induce no or little organ or cell overload or pathological processes caused by such overload or other adverse effects in vivo.

Various examples of biodegradable polymer materials are known in the art, any of which are generally suitable for use in the polymer coating of the present invention. Examples of polymers that are considered to be biodegradable include aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, polycarbonates, naturally-occurring biodegradable polymers such as chitosan, collagen, starch, and blends thereof. Examples of polyortho esters include a polylactide, a polyglycolide, a polycaprolactone, a polylactic acid, a biodegradable polyamide, a biodegradable aliphatic polyester, and/or copolymers thereof or with other biodegradable polymers such as those mentioned above. Illustrative examples of biodegradable polymers include, but are not limited to a polylactide such as poly(L-lactide) (PLLA), a polycaprolactone (PCL), a copolymer of polycaprolactone (PCL) and polylactic acid (PLA), or a copolymer of poly(lactide) and poly(glycolide) (PLGA). More specific examples of copolymers which can used in the present invention include copolymers of polycaprolactone (PCL) and polylactic acid (PLA) having an glycolide content of about 5-60%, 5-55%, 5-50%, 10-50%, 15-50%, or 20-50%, or approximately 20%, 25%, 30%, 35%, or 50%, or a copolymer of poly(lactide) and poly(glycolide) (PLGA) having an glycolide content of about 5-50%, 10-50%, 15-50%, or 20-50%, or approximately 20%, 25%, 30%, 35%, or 50%, based on the copolymer composition.

In the context of the present invention, "plasticizer" generally means a substance added to a polymer material to soften it and to improve flexibility. More particularly, the plasticizer as used according to the present invention can preferably lower the glass transition temperature, Tg, the modulus, i.e. increases the elongation at break, or changes the crystalline behavior of a polymer material. Any known plasticizer can be used in the polymer layer as long as the plasticizer provides the polymer layer with the above-mentioned properties. The plasticizer may also be biocompatible, especially non-toxic. However, due to the small amount of plasticizer used compared to the entire body mass of a patient, use of a plasticizer that may have some adverse effects on the human body is also within the scope of the invention. Some illustrative examples of plasticizer that can be used in the present invention include, but are not limited to triethyl citrate (TEC), polyalkylene glycols such as polyethylene glycols (PEG) or polypropylene glycols, propylene glycol (PG) glycerol, di-2-ethylhexyladipate (dioctyladipate), di-2-ethylhexylphthalate (dioctylphthalate), dicyclohexylphthalate; diisononyladipate; diisononylphthlate; n-butyl benzyl phthalate, 1,3-butylene glycol/adipic acid polyester (1700-2200 MW) containing 16 weight percent terminal myristic, palmitic and stearic acid ester functionality. Other examples of plasticizers include epoxidized butyl esters of linseed oil fatty acid, epoxidized linseed oil or epoxidized soya oil. Examples of polyalkylene glycols include low molecular weight (MW) compounds (for example polyethylene glycols (PEG) or polypropylene glycols) having an MW of about 60-about 8000, or about 100-6000, about 100-5000, about 100-4000, or about 150-2000. Illustrative examples include diethylene glycol, triethylene glycol, dipropylene glycol, or tripropylene glycol, to name only a few.

The amount of plasticizer is not limited but is generally adjusted such that the biodegradable polymer coating maintains mechanical integrity during its use, including for example, during the storage and upon balloon expansion, even if drugs, which may be contained in the coating layer and which can also affect the physical properties of the coating layer, are present. In some embodiments of the invention, the plasticizer can be contained in one or all of the polymer layers in an amount of about 1-about 30 wt %, or about 1-25 wt %, about 2-25 wt %, about 3-25 wt %, about 4-25 wt %, about 5-25 wt %, about 6-25 wt %, about 2-20 wt %, about 3-20 wt %, about 4-20 wt %, or about 5-20 wt %, based on the dry weight of the polymer layer. In line with above, the amount of plasticizers can for example be about 1, 2, 3, 4, 5, 6, 7, 8, 9, 10, 12, 15, 17, 19, 21, 23, 25, 27, or 29 wt %, based on dry weight of the respective layer of the polymer coating (i.e. the coating includings if more than one layer of the biodegradable polymer, each layer can contain the plasticizer in the weight range given here).

In the context of the present invention, the term "drug" generally means a therapeutic or pharmaceutical agent which can be included/mixed into the coating composition, or impregnated or incorporated into the coating in order to provide a drug-containing coating. The drug in the drug-containing coating can be any therapeutic or pharmaceutical agent suitable for use in drug-containing coatings for stents. Various examples include, but are not limited to: antiproliferative/antimitotic agents including natural products such as vinca alkaloids (e.g. vinblastine, vincristine, and vinorelbine), paclitaxel, epipodophyllotoxins (e.g. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiproliferative/antimitotic alkylating agents such as nitrogen mustards (such as mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase); antiplatelet (such as aspirin, dipyridamole, ticlopidine, clopidogrel, abciximab); antimigratory; antisecretory (such as breveldin); antiinflammatory: such as adrenocortical steroids (cortisol, cortisone, fludrocortisone, prednisone, prednisolone, 6-alpha-methylprednisolone, triamcinolone, betamethasone, and dexamethasone), non-steroidal agents (such as salicylic acid derivatives e.g. aspirin); para-aminophenol derivatives (e.g. acetaminophen); indole and indene acetic acids (such as indomethacin, sulindac, and etodalac), heteroaryl acetic acids (such as tolmetin, diclofenac, and ketorolac), arylpropionic acids (such as ibuprofen and derivatives), anthranilic acids (such as mefenamic acid, and meclofenamic acid), enolic acids (such as piroxicam, tenoxicam, phenylbutazone, and oxyphenthatrazone), nabumetone, gold compounds (such as auranofin, aurothioglucose, gold sodium thiomalate); immunosuppressive (such as cyclosporine, tacrolimus (FK-506), sirolimus (rapamycin), azathioprine, mycophenolate mofetil); angiogenic such as vascular endothelial growth factor (VEGF), fibroblast growth factor (FGF); nitric oxide donors; anti-sense oligo nucleotides and combinations thereof.

In some embodiments of the invention, the anti-thrombotic drug can, for example, be selected from the group consisting of small organic molecules such as clopidogrel, triflusal, or analog salicylic acid derivatives or a protein such as hirudine or thrombin. Illustrative examples of an anti-restenotic drug are sirolimus, also called rapamycin paclitaxel, and evolimus.

Another example of a therapeutic agent that may be used in the stent coating is the compound known as elarofiban (b-[[[(3R)-1-[1-oxo-3-(4-piperidinyl)propyl]-3-piperidinyl] carbonyl]amino]-3-pyridinepropanoic acid, (bS)-(9CI), RWJ-53308) and elarofiban analogs that are described in International patent application WO 2005/087266.

In this context, it is noted that the drug (therapeutically active agent) to be incorporated into one or more of the layers of the coating can be a small organic molecule, a protein or a fragment of the protein, a peptide or a nucleic acid such as DNA or RNA. The term "small organic molecule" as used herein typically denotes an organic molecule comprising at least two carbon atoms, but preferably not more than 7 or 12 rotatable carbon bonds, having a molecular weight in the range between 100 and 2000 Dalton, or between 100 and 1000 Dalton, that optionally can include one or two metal atoms. The term "peptide" as used herein typically refers to a dipeptide or an oligopeptide with 2-about 40, 2-about 30, 2-about 20, 2-about 15, or 2-about 10 amino acid residues. The peptide may be a naturally occurring or synthetic peptide and may comprise—besides the 20 naturally occurring L-amino acids—D-amino acids, non-naturally occurring amino acids and/or amino acid analogs. With "protein" is meant any naturally occurring polypeptide that comprises more than 40 amino acid residues. The protein can be a full length protein or a truncated form, for example, an active fragment. Illustrative examples of proteins include, but are not limited to antibodies or other binding proteins with antibody like properties (for example, affibodies or lipocalin muteins knows as "Anticalins®") for selected cell receptors, growth factors such as VEGF (Vascular Endothelial Growth Factor) and similar factors for transmitting signals, cardiovascular therapeutic proteins or cardiac hormones and active fragments thereof or prohormones or preprohormones of such cardiac hormones (these hormones or the prohormones can either be peptides as defined herein, if they have less than 40 amino acid residues, or a protein, should their polypeptide sequence contain more the 40 amino acid residues). Further examples for cardiovascular therapeutic agents can be peptides or DNA such as the DNA for nitric oxide. Examples of nucleic acid molecules include sense or anti-sense DNA molecules (if expression of a target gene is to be controlled) or the coding sequence (either alone or in gene-therapy vector, for example) of a therapeutically active protein that is to be produced. In such a case, the nucleic acid may code for a protein that promotes wound healing as described in International patent application WO 97/47254, for example.

Figure 1A:
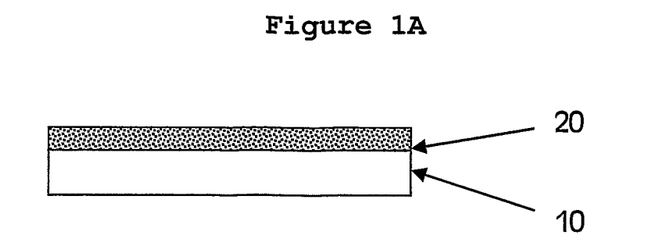
FIG. 1A shows a first embodiment of a stent of the present invention having a single polymer layer structure.

In an embodiment of the first aspect of the invention which is illustrated in FIG. 1A, the non-biodegradable stent of the invention comprises a non-biodegradable support (10) and bio-degradable polymer coating which is made of a single polymer layer (20) comprising said polymer and said plasticizer.

In this embodiment, the plasticizer contained in the polymer layer can be present in an amount sufficient to adjust the glass transition temperature (Tg) of the single polymer layer in the range of about 10-40° C., or in the range of about 25-40° C., or about 25-37° C., or about 25-35° C., or about 30-35° C., and/or the elongation at break in the range of more than 150% to less than 1000%, or between 200% and 500%. In case, the polymer is present in the polymer layer in a semi-crystalline or crystalline state, i.e., is rigid at ambient temperatures such as of 28-40° C., the plasticizer may affect the crystallinity of the polymer layer more than the transition temperature Tg. For example, the Tg of pure PCL coatings is about −30° C. and, thus, the addition of a plasticizer lowers the rigidity or stiffness of the polymer layer because of the change of the crystalline state of the polymer, but not by lowering the Tg.

Polymer layers of this embodiment may comprise a polymer composition made of a poly caprolactone (PCL) or a poly caprolactone-polylactic acid PCL-PLA co-polymer (lactic acid (LA) content of 5-60%) or a poly(lactide) and poly(glycolide) co-polymer (PLGA) (glycolic acid (GA) content of 5-50%), wherein a plasticizer is comprised in an amount sufficient to provide the desired physical properties. The plasticizer may, for example, be present in an amount of 1-30 wt %, based on the dry weight of the polymer layer. An amount of lower than 1 wt % might not be sufficient to maintain the mechanical integrity of the coating after stent expansion using a balloon and an amount of more than 30 wt % would make the polymer flow and could lead to effects such as the so-called "webbing" between the struts of a stent etc.

The single polymer layer may optionally comprise one or more drugs, for example, for preventing restenosis or the like. All drugs or therapeutic agents mentioned above can be used alone or in any combination thereof in the polymer layer of this embodiment of the invention. If a drug is contained, the drug can be incorporated into the polymer layer by admixing, impregnating, or the like, wherein the drug does not necessarily need to be uniformly distributed within the polymer layer.

Illustrative examples of drugs that may be used in the one or more polymer layer of the coating of the non-biodegradable stents of the present invention are anti-thrombotic, anti-inflammatory, anti-restenoic or immunodepressive drugs. In this context, it is noted that the drug to be incorporated into one or more of the layers of the coating can be a small organic molecule, a protein or a fragment of the protein, a peptide or a nucleic acid such as DNA or RNA.

Illustrative examples of the anti-thrombotic drug can, for example, be selected from the group consisting of small organic molecules such as clopidogrel, triflusal, or analog salicylic acid derivatives or a protein such as hirudine or thrombin. Illustrative examples of an anti-restenotic drug are sirolimus, also called rapamycin paclitaxel, and evolimus. As mentioned above, other therapeutic agents such as peptides, proteins or DNA can also be used in coated stents of the invention.

The amount of the drug (or 2 or more drugs together) in one or more layers of the coating is not limited and can be as high as desired as long as the physical properties of the polymer coating, especially the glass transition temperature and the elongation at break or the crystallinity, are not adversely affected. In some embodiments, the amount of the drug, based on the dry weight of the polymer layer that contains the drug, may be up to about 35 wt %. The drug may be present in an amount of 0.1 to 35 wt %, 1 to 35 wt % or 1 to 10, 15, 20, 25 or 30 wt % based on the dry weight of the polymer layer that contains the drug. In some embodiments the amount of the drug is about 2-20 wt %, for example, in case the drug is an anti-thrombotic drug. In embodiments, where an anti-restenotic drug is used, such drug may be present in an amount of about 3-26 wt % or 5-25 wt %, for example. In this context, it is again noted that it is possible to include more than one drug of the same or different type into a coating layer, for example, an anti-restenotic drug and an anti-inflammatory drug or two anti-thrombotic drugs.

Figure 1B:
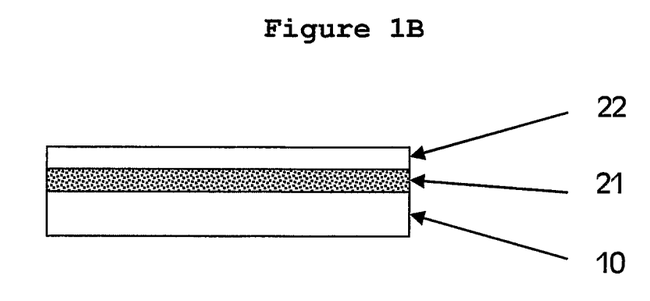
FIG. 1B shows a second embodiment of a stent of the present invention having a multiple layer structure of the coating.

In another embodiment of the first aspect of the invention which is shown in FIG. 1B, the non-biodegradable stent of the invention includes a stent support (exemplified by reference number 10 in FIG. 1B) and a biodegradable polymer coating comprising:

i) a first polymer layer (exemplified by reference number 21 in FIG. 1B) comprising a biodegradable polymer and a plasticizer, and ii) a second polymer layer (exemplified by reference number 22 in FIG. 1B) comprising a biodegradable polymer.

In this embodiment, the composition of the first polymer layer (21) enables the first coating layer to maintain coating integrity after stent expansion without the need for a primer coating. The polymer layer may have the same polymer composition as in the single layer embodiment described above. The plasticizer contained in the polymer layer is present in an amount sufficient to adjust the glass transition temperature (Tg) of the first polymer layer in the range of about 10-40° C., or in the range of about 25-40° C., or about 25-37° C., or about 25-35° C., or about 30-35° C., and/or the elongation at break in the range of more than 150% to less than 1000%, or between 200% and 500%. In case, the polymer is present in the polymer layer in a semi-crystalline or crystalline state, i.e., is rigid at ambient temperatures such as of 28-40° C., the plasticizer may affect the crystallinity of the polymer layer more than the transition temperature Tg. For example, the Tg of pure PCL coatings is about −30° C. and, thus, the addition of a plasticizer lowers the rigidity or stiffness of the polymer layer because of the change of the crystalline state of the polymer.

Some embodiments of the first polymer layer comprise a polymer composition made of a poly caprolactone (PCL) or a poly caprolactone-polylactic acid PCL-PLA co-polymer (lactic acid (LA) content of 5-60%) or a poly(lactide) and poly(glycolide) co-polymer (PLGA) (glycolic acid (GA) content of 5-50%). Also in these embodiments the plasticizer is comprised in an amount sufficient to provide the desired physical properties, for example in an amount of 1-30 wt %, based on the dry weight of the polymer layer. Illustrative examples of plasticizers that may be used include, but not are limited to triethyl citrate (TEC), low molecular weight polyalkylene glycols such as polyethylene glycol (PEG), or propylene glycol (PG), or glycerol.

Illustrative embodiments of polymer compositions of the first polymer layer (21) are the following:

PLGA 50/50 (i.e, 50% LA and 50% GA) with 1-10% plasticizer such as TEC;
PLGA 65/35 (i.e, 65% LA and 35% GA) with 2-15% plasticizer such as TEC;
PLGA 75/25 (i.e, 75% LA and 25% GA) with plasticizer such as 2-15% TEC; and
PLGA 80/20 (i.e, 80% LA and 20% GA) with plasticizer such as 5-15% TEC.

The mechanical properties of the PLGA 50/50, 75/25 and 80/20 polymers are as follows:

|  | PLGA 50/50 | PLGA 50/50 with 5% TEC | PLGA 50/50 with 10% TEC |
|---|---|---|---|
| Tg | 45.8° C. | 31.8° C. | 28.8° C. |
| Elongation-to-break | 16% | 240% | 290% |
| Modulus | 2550 MPa | 1440 MPa | 785 MPa |

|  | PLGA 75/25 | PLGA 75/25 with 5% TEC | PLGA 50/50 with 10% TEC |
|---|---|---|---|
| Tg | 40.3° C. | 34.6° C. | 28.3° C. |
| Elongation-to-break | 150% | 300% | 420% |
| Modulus | 1700 MPa | 1260 MPa | 800 MPa |

|  | PLGA 80/20 | PLGA 80/20 with 5% TEC | PLGA 80/20 with 10% TEC |
|---|---|---|---|
| Tg | 46.2° C. | 44.6° C. | 34.9° C. |
| Elongation-to-break | 50% | 250% | 295% |
| Modulus | 2220 MPa | 2250 MPa | 1420 MPa |

The polymer coatings have a sufficient overall coating quality and, especially a sufficient mechanical integrity of the coating, because of the first polymer layer, i.e. the polymer layer which is directly coated on the non-biodegradable stent, comprises a plasticizer or has the specific physical properties such as a specific Tg or elongation at break as discussed above.

The composition of the second polymer layer (22) may be identical to the composition of the first polymer layer or can be made of the same polymer composition as the first polymer layer but with or without incorporating a plasticizer. The same plasticizer or a different one as used in the first polymer layer can generally be used, wherein illustrative examples include, but not are limited to triethyl citrate (TEC), propylene glycol (PG), or glycerol. If a plasticizer is added to the second polymer layer, the plasticizer content may be the same as in the first polymer layer in order to sufficiently adjust the physical, properties of this layer within the ranges as in the first layer. The plasticizer can be present in the second polymer layer in an amount of about less than 30 wt %, based on the dry weight of the second polymer layer.

Illustrative embodiments of compositions for the second polymer layer (22) of the biodegradable coating are:

PLGA 80/20 with 2-10% TEC,
PLGA 75/25 with 2-10% TEC,
PLLA 96/4 with 2-20% TEC, and
PLLA with 5-20% TEC.

Optionally, the first and the second polymer layers (21; 22) may comprise one or more drugs as defined in the single layer embodiment. If a drug is contained, the drug can be incorporated into the polymer layers by admixing, impregnating, or the like, wherein the drug does not necessarily need to be uniformly distributed within the polymer layers.

The drug amount in the first and second polymer layer, respectively, is not limited and can be as high as desired as long as the physical properties of the polymer coating, especially the glass transition temperature and the elongation at break or the crystallinity, are not adversely affected. In some embodiments, the amount of the drug, based on the dry weight of the respective polymer layer, may be up to about 35 wt %. The drug may be present in an amount of 0.1 to 35 wt %, 1 to 35 wt % or 1 to 10, 15, 20, 25 or 30 wt % based on the dry weight of the polymer layer that contains the drug. In some embodiments the amount of the drug is about 2-20 wt %, for example, in case the drug is an anti-thrombotic drug. In embodiments, where an anti-restenotic drug is used, such drug may be present in an amount of about 3-26 wt % or 5-25 wt %, for example. In this context, it is again noted that it is possible to include more than one drug of the same or different type into a coating layer, for example, an anti-restenotic drug and an anti-inflammatory drug or two anti-thrombotic drugs.

In another embodiment of the first aspect of the invention which is also shown in FIG. 1B, the non-biodegradable stent of the invention includes a stent support (exemplified by reference number 10 in FIG. 1B) and a biodegradable polymer coating comprising:
i) a first polymer layer (exemplified by reference number 21 in FIG. 1B) comprising a biodegradable polymer, and
ii) a second polymer layer (exemplified by reference number 22 in FIG. 1B) comprising a biodegradable polymer and a plasticizer.

In this embodiment, the composition of the second polymer layer (21) enables the whole polymer coating, i.e. the first and the second polymer layer, to maintain coating integrity after stent expansion without the need for a primer coating.

The first polymer layer may have the same polymer composition as in the single layer embodiment described above, wherein optionally a drug and/or a plasticizer may be contained in the polymer layer in an amount sufficient to adjust the glass transition temperature (Tg) of the single polymer layer in the range of about 10-40° C., or in the range of about 25-40° C., or about 25-37° C., or about 25-35° C., or about 30-35° C., and/or the elongation at break in the range of more than 150% to less than 1000%, or between 200% and 500%.

Some embodiments of the first polymer layer comprise a polymer composition made of a poly caprolactone (PCL) or a poly caprolactone-polylactic acid PCL-PLA co-polymer (lactic acid (LA) content of 5-60%) or a poly(lactide) and poly(glycolide) co-polymer (PLGA) (glycolic acid (GA) content of 5-50%). Also in these embodiments, if necessary, a plasticizer may optionally be comprised in an amount sufficient to provide the desired physical properties, for example in an amount of 1-30 wt %, based on the dry weight of the polymer layer. Illustrative examples of plasticizers that may be used include, but not are limited to triethyl citrate (TEC), low molecular weight polyethylene glycol (PEG), propylene glycol (PG), glycerol etc.

The composition of the second polymer layer (22) may be identical to the composition of the first polymer layer or can be made of the same polymer composition as the first polymer layer but contains one or more plasticizers. The same plasticizer or a different one as used in the polymer layer of the single polymer layer embodiment can generally be used, wherein illustrative examples include, but are not limited to triethyl citrate (TEC), low molecular weight polyethylene glycol (PEG), propylene glycol (PG), glycerol etc. In some embodiments, the plasticizer content in the second polymer layer may be the same as in the polymer layer of the embodiment having a single polymer layer in order to sufficiently adjust the physical, properties of the overall coating. The plasticizer can, for example, be present in the second polymer layer in an amount of more than about 1 wt % to less than about 30 wt %, or in an amount of about 1 to 25 wt %, about 2-25 wt %, about 3-25 wt %, about 4-25 wt %, about 5-25 wt %, about 6-25 wt %, about 2-20 wt %, about 3-20 wt %, about 4-20 wt %, or about 5-20 wt %, based on the dry weight of the second polymer layer. The polymer coatings have a sufficient overall coating quality and, especially a sufficient mechanical integrity of the coating, because a plasticizer is present in the second polymer layer and, thus, has specific physical properties such as a specific Tg or elongation at break as discussed above.

Figure 1C:
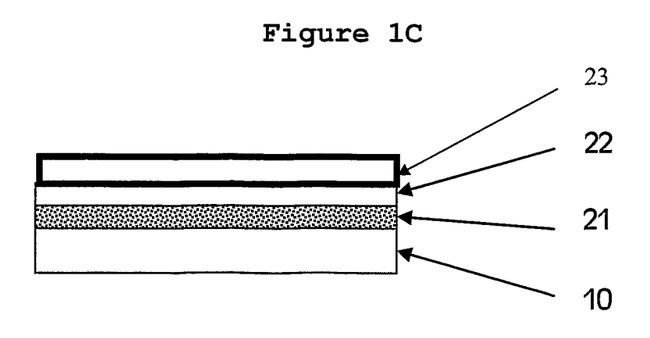
FIG. 1C shows a further embodiment of a stent of the present invention having a multiple layer structure of the coating wherein a topcoat layer is provided as the outermost layer.

In another embodiment of this aspect of the invention which is shown in FIG. 1C, the two-layer embodiment can be modified by adding one or more additional layers (exemplified by reference number 23 in FIG. 1C, in case only one additional layer is present) comprising a biodegradable polymer. For example, a topcoat layer can be added as additional layer (23) wherein the top coat layer may comprise the same or a different biodegradable polymer as in the first or second polymer layers (21; 22). The top coat layer is then provided on the second polymer layer (i.e. in a three-layer coating) or on one of the additional layers in a multi-layer system (such as a coating comprising four, five, six, etc. layers) as the outermost layer. The plasticizer may only be present in the top coat layer, with the other layers each containing one drug for example. Alternatively, one or more of the "drug loaded" layers may include a plasticizer. It is however also possible that the top coat does not contain a plasticizer but only for example, the layer that directly contacts the stent or only the first and the second layer contains the plasticizer (for example, in case of a three layer arrangement such as one where the first layer contain a drug such as sirolimus, the second layer contains a drug such as triflusal).

In an illustrative example of this (multilayer) embodiment, the biodegradable polymer in the topcoat layer (23) may be selected from the group of poly(L-lactide) (PLLA), polycaprolactone (PCL), a copolymer of polycaprolactone (PCL) and polylactic acid (PLA) having an lactic acid content of 5-60%, a copolymer of poly(lactide) and poly(glycolide) (PLGA) having an glycolide content of 5-60%.

As mentioned, analogously to the first and second polymer layer, a plasticizer can also be added to the topcoat layer. The plasticizer can be the same or a different one as in the first and/or second polymer layer and may be selected from the group consisting of triethyl citrate (TEC), propylene glycol (PG), and glycerol.

If the stent of the first aspect of the invention comprises a drug, the drug may be loaded into the single polymer layer or the first and/or second and/or any further polymer layers such as a topcoat layer. The same or different drugs as in the first and/or second polymer layer can be used in each of the layers. Illustrative examples of the drug are, for example, an anti-thrombotic, anti-inflammatory, anti-restenotic, or immunodepressive drug. Specific examples of the anti-thrombotic drug include clopidogrel, triflusal, and analog salicylic acid derivatives. Specific examples of the anti-restenotic drug include sirolimus and everolimus.

Also in this embodiment, the drug(s) may be present in an amount of 0.1 to 35 wt %, 1 to 35 wt % or 1 to 10, 15, 20, 25 or 30 wt % based on the dry weight of the polymer layer that contains the drug. In some embodiments the amount of the drug is about 2-20 wt %, for example, in case the drug is an anti-thrombotic drug. In embodiments, where an anti-restenotic drug is used, such drug may be present in an amount of about 3-26 wt % or 5-25 wt %, for example.

In some embodiments of the first aspect of the invention, drug combinations of one or more of the above-mentioned drugs can be comprised in the polymer layer. A specific example is a combination of two or more drugs including at least an anti-thrombotic and an anti-restenotic drug. In one particular embodiment, the coating comprises a drug combination of trifusal in an amount of about 1-15 wt % and sirolimus or a sirolimus derivative in an amount of 1-15 wt %, based on the dry weight of the respective drug containing layer.

In an illustrative embodiment of the first aspect of the invention, the non-biodegradable stent includes a non-biodegradable stent support (20) and a polymer coating comprising a first polymer layer (21) and a second polymer layer (22). In this embodiment the first polymer layer contains a specific drug amount wherein the second polymer layer (22) is drug free. When covering the drug-containing first polymer layer (21) with a drug free polymer layer (22), the drug release characteristic can be controlled such that the drug is released over a longer time than without a drug-free second polymer layer (22). For example, the drug release can be sustained to about more than 2 months or more preferably to about 4 to 5 months. The same advantageous effect will be achieved with an embodiment containing more than two polymer layers, if the outermost layer, i.e. the topcoat layer (23), is provided as a drug free polymer layer.

The biodegradable polymer coating including at least one biodegradable polymer layer comprising a polymer and a plasticizer according to the first aspect of the invention may have an overall coating thickness in the range of about 5-30 microns, or in the range of about 7-15 microns. Overall coating thickness means the thickness of the single polymer layer or the thickness of the first, second or additional polymer layers in total.

In general, advantages of the biodegradable coatings of the present invention are the following:
The overall coating layer, i.e. all polymer layers, is biodegradable.
The incorporation of the drugs in the amounts as indicated does not compromise the mechanical integrity of the coating and does not affect the drug release control.
Each drug's release is separately controllable over several months, in particular over more than 2 months.
The overall coating thickness can be reduced and preferably ranges from about 7-15 microns.

In this context, it is noted that a stent of the invention can of course have any dimensions and that these dimensions mainly depend on the intended use of the stent, for example, when used in angioplasty to restore an adequate blood flow to the heart or in applications in the urethra tract. For purely illustrative purpose, (coated) stents with the following parameters may be used for angioplasty:

aspect are provided in an organic solvent and coated onto the stent in one or more consecutive steps to produce the at least one biodegradable polymer layer either by usual coating, spraying or dipping techniques. Thereafter, the stent can be dried. Each known drying method can generally be used in the present invention. Illustrative examples of drying methods are drying the coated stents in a vacuum oven or in a hot air oven. In one embodiment the coated stent is dried until the residual solvent levels of the coating are less than about 5%, or less than about 3%, or less than about 2%, or less than about 1%.

Illustrative examples of solvents for dissolving the polymer composition include, but are not limited, organic solvents such as hydrocarbons (e.g. pentane, hexane, cyclohexane, etc.), ethers (diethylether, tetrahydrofurane, dioxane, etc.), esters including diethylester etc, halogenated organic solvents such as chloroform, dichloromethane, dichloroethane, etc., or aromatic hydrocarbons (e.g. benzene, toluene, etc.).

In one embodiment of the coating method of the invention, the coating of a stent is optimized by either rotating the stent at different speeds during the coating or by atomizing a solution and spraying said solution at various distances from the stent. Both methods (rotating the stent at different speeds and atomizing a solution and spraying the solution) can also be combined with each other in order to further improve uniformity of the coating.

In the following the present invention will be described by specific examples, which are not described to limit the scope of the present invention to these particular embodiments, but should merely explain the present invention.

EXAMPLES

Example 1

In the first example, up to 20% of sirolimus were incorporated into poly (lactide-co-glycolide) with about 80% lactide, which also contains 5% by weight of triethyl citrate (TEC) as plasticizer. This formulation was then coated onto

| Stent model | Diameter of stent (mm) | Expanded diameter (mm) | Diameter of strut (W × T) μm | Length of stent (mm) | Projected area (mm²/mm) | Total surface area (mm²/mm) | Total surface area (mm²/stent) |
|---|---|---|---|---|---|---|---|
| CoCr MV stent (Major Vessel) | 1.75 | 3.0-3.5 | 83 × 92 | 12 | 1.35 | 5.92 | 68.08 |
| CoCr SV stent (Small Vessel) | 1.5 | 2.0-2.5 | 75 × 80 | 12 | 1.203 | 5.44 | 62.56 |
| Stainless steel | 1.75 | 3.-3.5 | 110 × 100 | 20 | | | |

In a second aspect of the invention, the invention relates to a method for manufacturing a coated non-degradable stent, wherein the method comprise coating the non-degradable stent support (10) with a mixture comprising a biodegradable polymer and a plasticizer in order to form at least one biodegradable polymer layer (20; 21, 22, 23).

In an embodiment of this aspect of the invention, the coating is carried out by spray coating or dip coating or any alternative conventional coating method, wherein a solution of a biodegradable polymer and a plasticizer as defined in any one of the afore-mentioned embodiments of the first a stent of a metal alloy (cobalt-chromium alloy) as a first polymer layer. As a second polymer layer, a layer of 50/50 PLGA was coated onto the first polymer layer without any drug content.

Both polymer layers gave a uniform coating that can control the release of the drug sirolimus over 2 months.

Example 2

10% of clopidogrel and 10% of sirolimus were incorporated into a coating layer having the configuration that schematically is shown in FIG. 1C. The same metal stent as in Example 1 was coated with a first polymer layer of PLGA 50/50 with 5 wt % TEC. Thereon a second polymer layer of PLGA 80/20 with 10 wt % clopidogrel was coated, followed by a drug-free layer of PLGA 75/25 with 5 wt % TEC.

All three polymer layers gave a uniform biodegradable drug-containing coating also having a sufficient drug release control capability.

Example 3

Testing of Stress-Strain Behavior

A calculated amount of PLGA (with about 20% GA content) was dissolved in dichloromethane, such that the solution viscosity is about 1000 poise or less. This was then divided into 3 parts:
  Part 1 was mixed with triethyl citrate (TEC) so that the final amount of TEC in the dried film was 5%.
  Part 2 was mixed with TEC so that the TEC amount is 10% by weight.
  Part 3 is used as such, without TEC addition.

The solutions were casted on glass slides using a knife-edged coater, set to a wet thickness of about 0.5 mm. The film was then dried overnight at 25° C., and then further dried in a vacuum oven for 7 days so that the residual solvent amount was less than 1%. The films were then clamped on an Instron® tensile tester and evaluated for stress-strain behavior at a constant rate of strain.

Figure 2:
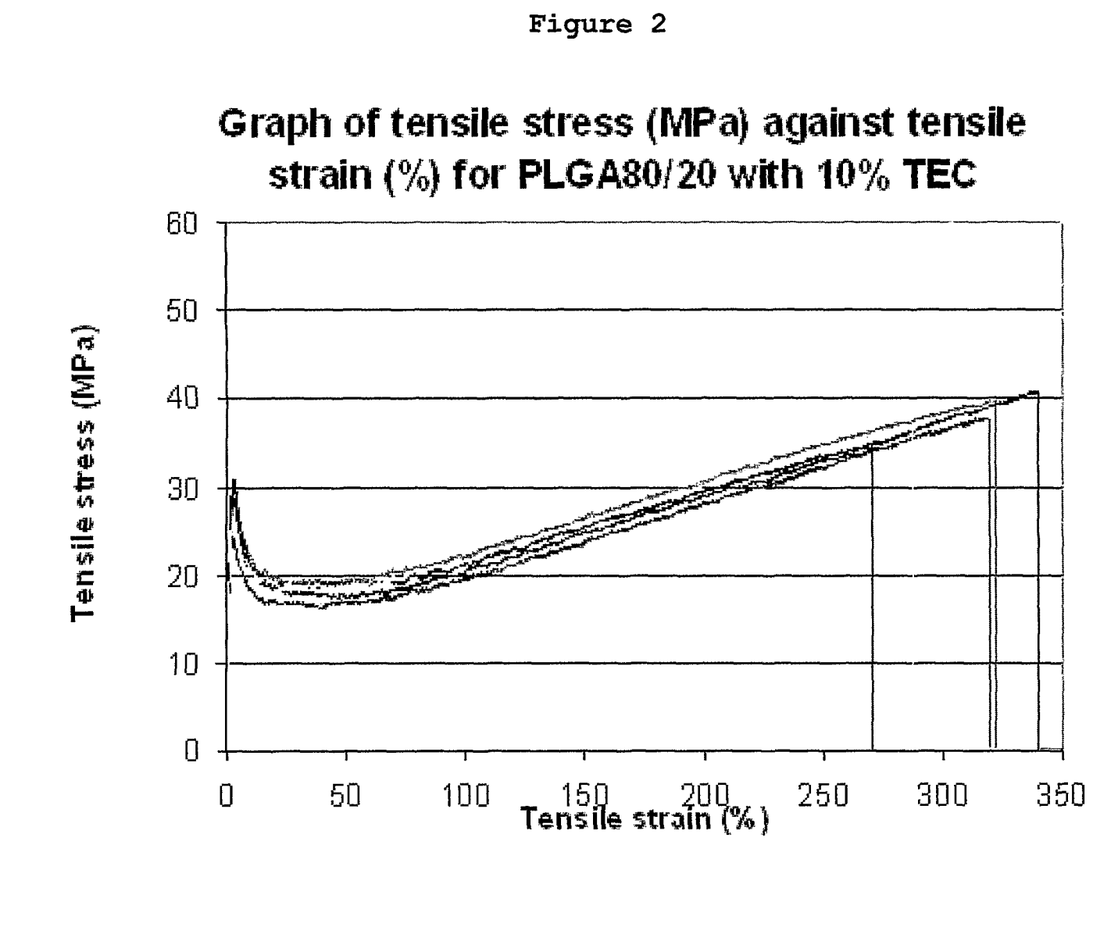
FIG. 2 shows a stress-strain behaviour plot at a constant rate of strain for several polymer PLGA 80/20 specimens (with 10% TEC).

A typical plot for several specimens (with 10% TEC) is shown in FIG. 2. The elongation at break is averaged over the several values on the X-axis intercepts of the perpendicular lines. In this example, the elongation at break ranges between 260% to about 330%

Similar plots for the 0% and 5% TEC samples yielded corresponding elongation at break values.

Coating the Stents

A concentrated solution of PLGA in chloroform was prepared, with or without added plasticizer (TEC, for example). Approximate amounts were 500 mg for PLGA and 60 mg of TEC in 50 mL of chloroform. A cobalt-chromium stent as used in Example 1 was cleaned ultrasonically in acetone and ethanol, and was then dried for 2 hours. The sprayer was loaded with the solution, and the solution was atomized and sprayed at various distances from the stent in order to optimize the coating. The stent was also rotated at different speeds to optimize the coating. The coated stent was then air dried for 12 hours, followed by drying in a vacuum oven for 2 weeks, until residual solvent levels were less than 1%.

Figure 3A:
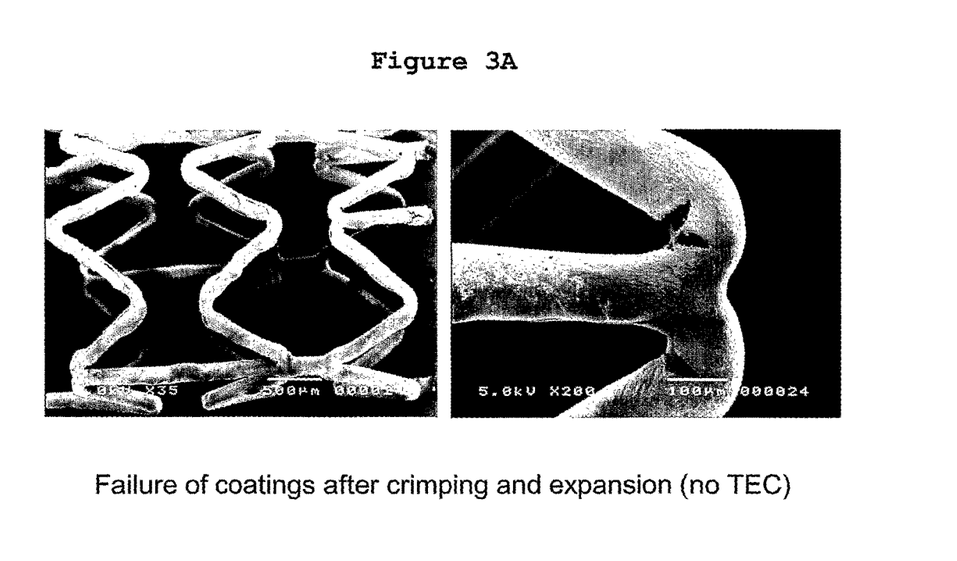
Figure 3B:
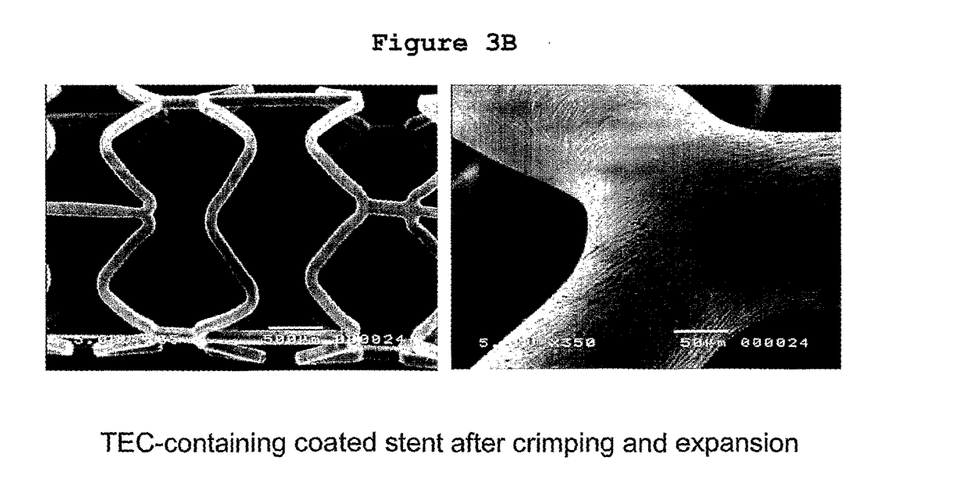

The coated stents were then balloon expanded and evaluated by a scanning electron microscope (SEM) for cracks, imperfections and webbing. As shown in FIG. 3, the plasticized composition had fewer imperfections and better mechanical integrity.

Evaluation of the Stents

Figure 4:
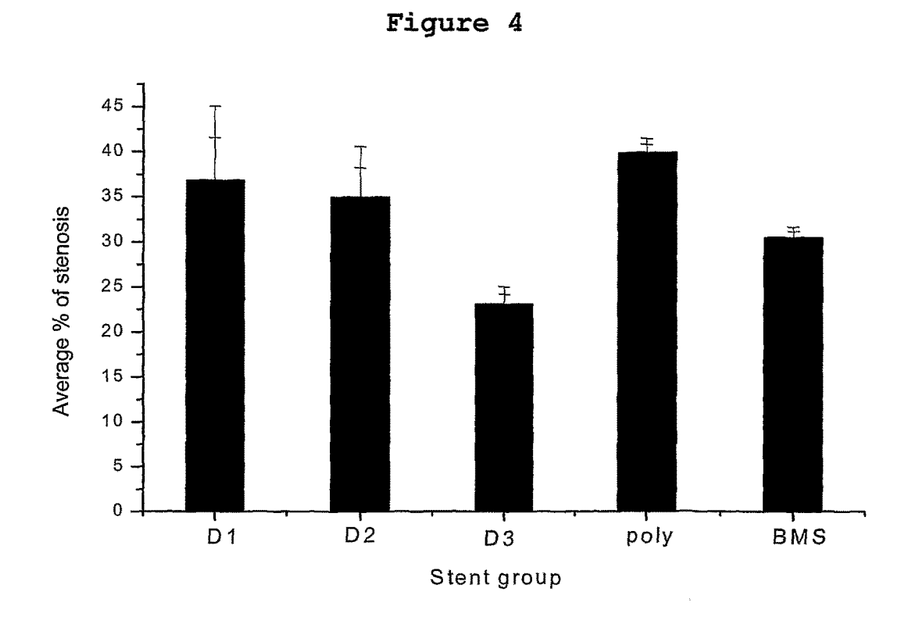
FIG. 4 shows a diagram showing the results of preventing stenosis in a 30-day animal study.

A 30-day animal study was carried out with the following stents:
  Bare Metal alloy Stent (BMS) made of a cobalt-chromium alloy
  BMS with Polymer Coating (PLGA 80/20 with 10% TEC, 2 layers)
  D1=Stent with 92.5 μg of sirolimus
  D2=Stent with 105.1 μg of sirolimus
  D3=Stent with 93.2 μg of sirolimus and 37.3 μg of triflusal The basic configuration of the coated stents was as shown in FIG. 1B, wherein the stent support (10) was a Co—Cr stent, the first polymer layer (21) was made of PLGA 80/20 with TEC and drug, and the second polymer layer (22) was a drug free PLGA 80/20 coating with TEC. The results are shown in FIG. 4.

In the 30-day study, it was found that the stented vessels were all patent, but with varying degrees of stenosis (blockage). This stenosis was the least for the stent (D3), which contained the drugs sirolimus and triflusal in combination.

This formulation which contains both drugs (D3) is statistically superior in reducing stenosis than the other formulations.

Example 4

Figure 5:
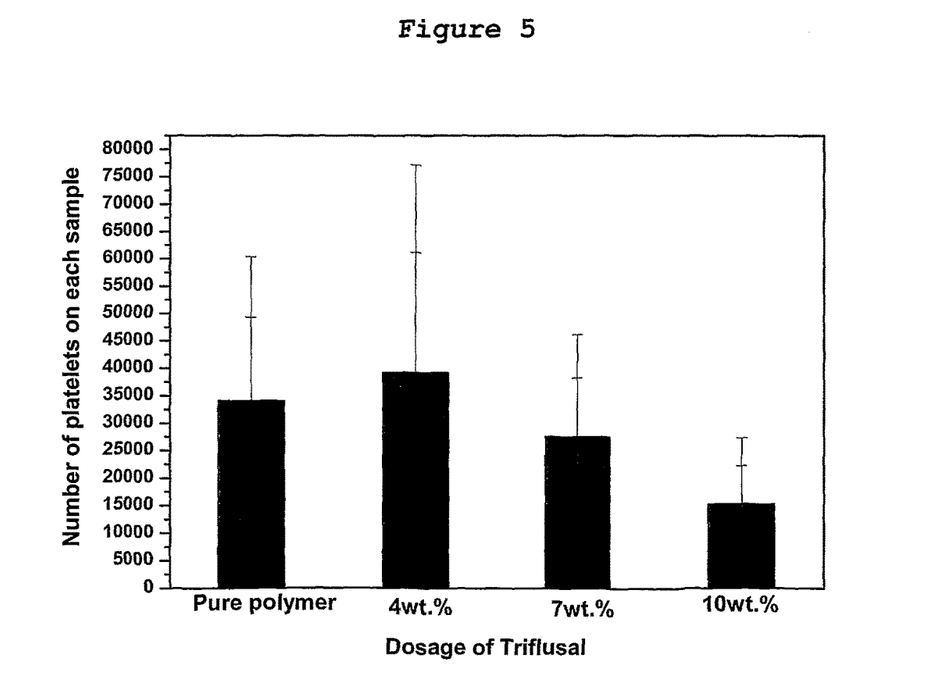
FIG. 5 shows the correlation between the dosage of triflusal and the number of platelet adhesion of polymer coated metal strips in an in vitro thrombogenicity experiment.

In Vitro Thrombogenicity Experiment:

Metal strips with coatings of PLGA 80/20 containing varying amounts of triflusal (4, 7 and 10 wt %) were tested for thrombogenicity/platelet adhesion using a dynamic method. Human blood was collected and anti-coagulated. Platelet rich plasma (PRP) was then prepared from the blood, and labeled with radioactive iodine, I-125. The test samples were exposed to this labeled PRP for 2 hours under perfusion at a flow rate of 40 mL min$^{-1}$. Radioscintigraphy was then used on the washed and rinsed metal-coated strips, to count the number of adhered platelets. The results are shown in FIG. 5.

Thus a 10% loading of triflusal is effective at reducing platelet adhesion, and hence thrombus formation.

Such compositions are therefore efficient at reducing stenosis in coronary arteries, compared to a bare metal or metal alloy stents, and to single dosages of sirolimus.

The listing or discussion of a previously published document in this specification should not necessarily be taken as an acknowledgement that the document is part of the state of the art or is common general knowledge. All documents listed are hereby incorporated herein by reference in their entirety for all purposes.

The invention has been described broadly and generically herein. Each of the narrower species and subgeneric groupings falling within the generic disclosure also form part of the invention. This includes the generic description of the invention with a proviso or negative limitation removing any subject-matter from the genus regardless of whether or not the excised material is specifically recited therein.

The invention illustratively described herein may suitably be practiced in the absence of any element or elements, limitation or limitations, not specifically disclosed herein. Thus, for any example, the terms "comprising", "including", "containing", etc. shall be read expansively and without any limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Additional objects, advantages, and features of this invention will become apparent to those skilled in the art upon examination of the foregoing examples and the appended claims. Thus, it should be understood that although the present invention is specifically disclosed by exemplary embodiments and optional features, modification and variation of the invention embodied therein herein disclosed may be resorted to by skilled in the art, and that such modifications and variations are considered to be within the scope of this invention. In addition, where features or aspects of the invention are described in terms of Markus groups, those skilled in the art will recognize that the invention is also thereby described in terms of any individual member or subgroup of members of the Markush group.

The invention claimed is:

1. A non-biodegradable stent comprising a biodegradable coating wherein said coating comprises one or more polymer layers comprising a biodegradable polymer and a plasticizer selected from the group consisting of triethyl citrate (TEC), a polyalkylene glycol, propylene glycol (PG) glycerol, di-2-ethylhexyladipate, di-2-ethylhexylphthalate, dicyclohexylphthalate, diisononyladipate, diisononylphthlate, n-butyl benzyl phthalate, and glycerol, wherein the plasticizer is contained in the one or more polymer layers in an amount from 1-30 wt %, based on dry weight of the one or more polymer layers, and wherein said coating comprises a drug combination of (i) triflusal and sirolimus or (ii) triflusal and a sirolimus derivative, the drug combination being present in an amount of about 0.1-35 wt %, based on dry weight of the drug containing layer.

2. The non-biodegradable stent of claim 1, wherein the non-degradable stent is made of a material selected from a metal, a metal alloy, and a biostable polymer.

3. The non-biodegradable stent of claim 2, wherein the alloy is a stainless steel or a cobalt chromium alloy.

4. The non-biodegradable stent of claim 1, wherein the biodegradable polymer coating is made of a single polymer layer comprising a biodegradable polymer and a plasticizer.

5. The non-biodegradable stent of claim 4, wherein the biodegradable polymer is selected from the group of poly(L-lactide) (PLLA), polycaprolactone (PCL), a copolymer of polycaprolactone (PCL) and polylactic acid (PLA) having an lactic acid content of 5-60%, a copolymer of poly(lactide) and poly(glycolide) (PLGA) having an glycolide content of 5-50%.

6. The non-biodegradable stent of claim 4, wherein the plasticizer is triethyl citrate.

7. The non-biodegradable stent of claim 4, wherein the plasticizer is contained in the polymer layer in an amount from 1-30 wt %, based on the dry weight of the polymer layer.

8. The non-biodegradable stent of claim 4, wherein the polymer is a PLGA copolymer and the plasticizer is contained in an amount from 2-15 wt %, based on the dry weight of the polymer layer.

9. The non-biodegradable stent of claim 4, wherein the polymer layer is made of a material having a glass transition temperature (Tg) in the range of about 10-40° C.

10. The non-biodegradable stent of claim 4, wherein the polymer layer is made of a material having an elongation at break in the range of more than 150% to less than 1000%.

11. The non-biodegradable stent of claim 1, wherein the biodegradable polymer coating comprises
(i) a first polymer layer comprising a biodegradable polymer and a plasticizer, and
(ii) a second polymer layer comprising a biodegradable polymer.

12. The non-biodegradable stent of claim 11, wherein the second polymer layer further comprises a plasticizer.

13. The non-biodegradable stent of claim 11, wherein the biodegradable polymer of the first polymer layer is selected from the group of poly(L-lactide) (PLLA), polycaprolactone (PCL), a copolymer of polycaprolactone (PCL) and polylactic acid (PLA) having an lactic acid content of 5-60%, a copolymer of poly(lactide) and poly(glycolide) (PLGA) having an glycolide content of 5-50%.

14. The non-biodegradable stent of claim 11, wherein the biodegradable polymer of the second polymer layer is selected from the group of poly(L-lactide) (PLLA), polycaprolactone (PCL), a copolymer of polycaprolactone (PCL) and polylactic acid (PLA) having an lactic acid content of 5-60%, or a copolymer of poly(lactide) and poly(glycolide) (PLGA) having an glycolide content of 5-50%.

15. The non-biodegradable stent of claim 11, wherein the plasticizer in the first and/or second polymer layer is triethyl citrate.

16. The non-biodegradable stent of claim 11, wherein the plasticizer is contained in the first polymer layer in an amount from about 1-30 wt % and in the second polymer layer in an amount of less than about 30 wt %, based on the dry weight of the respective first or second polymer layers.

17. The non-biodegradable stent of claim 11, wherein in the first polymer layer the polymer is a PLGA copolymer, and the plasticizer is contained in this layer in an amount from 2-15 wt %, based on the dry weight of the first polymer layer.

18. The non-biodegradable stent claim 11, wherein in the second polymer layer the polymer is a PLGA copolymer, and the plasticizer is contained in this layer in an amount from 2-10 wt %, based on the dry weight of the second polymer layer.

19. The non-biodegradable stent of claim 11, wherein in the second polymer layer the polymer is a PLLA, and the plasticizer is contained in this layer in an amount from 2-20 wt %, based on the dry weight of the second polymer layer.

20. The non-biodegradable stent of claim 11, wherein the polymer coating further comprises a topcoat layer comprising a biodegradable polymer.

21. The non-biodegradable stent of claim 1, wherein the amount of triflusal is about 1-15 wt % and the amount of sirolimus or a sirolimus derivative is about 1-15 wt %, based on dry weight of the drug combination containing layer.

22. The non-biodegradable stent of claim 11, wherein the first and second polymer layer is made of a material having a glass transition temperature (Tg) in the range of 10-40° C.

23. The non-biodegradable stent of claim 11, wherein the first and second polymer layer is made of a material having an elongation at break in the range of more than 150% to less than 1000%.

24. The non-biodegradable stent of claim 20, wherein the biodegradable polymer in the topcoat layer is selected from the group of poly(L-lactide) (PLLA), polycaprolactone (PCL), a copolymer of polycaprolactone (PCL) and polylactic acid (PLA) having an lactic acid content of 5-60%, a copolymer of poly(lactide) and poly(glycolide) (PLGA) having an glycolide content of 5-50%.

25. The non-biodegradable stent of claim 20, wherein the topcoat layer further comprises a plasticizer.

26. The non-biodegradable stent of claim 25, wherein the plasticizer is selected from the group consisting of triethyl citrate (TEC), a polyalkylene glycol, propylene glycol (PG) glycerol, di-2-ethylhexyladipate (dioctyladipate), di-2-ethylhexylphthalate (dioctylphthalate), dicyclohexylphthalate; diisononyladipate; diisononylphthlate; n-butyl benzyl phthalate.

27. The non-degradable stent of claim 1, wherein the drug combination is loaded into a single polymer layer or the first and/or second and/or any further polymer layers.

28. The non-biodegradable stent of claim 1, wherein the overall coating thickness ranges from about 5-30 microns.

* * * * *

UNITED STATES PATENT AND TRADEMARK OFFICE
CERTIFICATE OF CORRECTION

PATENT NO. : 9,987,399 B2
APPLICATION NO. : 12/740638
DATED : June 5, 2018
INVENTOR(S) : Subramanian Venkatraman et al.

It is certified that error appears in the above-identified patent and that said Letters Patent is hereby corrected as shown below:

In the Claims

Claim 26, Column 18, Line 59; replace the term "phthalate." with --phthalate, and glycerol.--.

Signed and Sealed this
Twenty-third Day of October, 2018

Andrei Iancu
*Director of the United States Patent and Trademark Office*